US 6,325,066 B1

(12) United States Patent
Hughes et al.

(10) Patent No.: US 6,325,066 B1
(45) Date of Patent: Dec. 4, 2001

(54) BLADDER AND BOWEL TRAINING SYSTEM WITH REMOVABLE VOICE MODULE SYSTEM

(76) Inventors: Charles B. Hughes, 3309 Lookout Dr., Huntsville, AL (US) 35801; Emory D. Hughes, 46 High Point Rd., Edgefield, SC (US) 29824

(*) Notice: Subject to any disclaimer, the term of this patent is extended or adjusted under 35 U.S.C. 154(b) by 0 days.

(21) Appl. No.: 09/206,596

(22) Filed: Dec. 7, 1998

Related U.S. Application Data

(63) Continuation-in-part of application No. 08/918,455, filed on Aug. 26, 1997, now Pat. No. 5,845,644.
(60) Provisional application No. 60/025,022, filed on Aug. 26, 1996.

(51) Int. Cl.[7] .................................................. A61F 5/48
(52) U.S. Cl. .................... 128/885; 128/886; 128/DIG. 26
(58) Field of Search .................................. 128/846, 885, 128/886, DIG. 25; 340/539, 573, 604, 620

(56) References Cited

U.S. PATENT DOCUMENTS

| | | | |
|---|---|---|---|
| 4,191,950 | * 3/1980 | Levin | 128/886 |
| 4,205,671 | * 6/1980 | Lassen | 128/886 |
| 4,977,906 | * 12/1990 | Di Scipio | 128/886 |
| 5,568,128 | * 10/1996 | Nair | 128/886 |
| 5,929,747 | * 7/1999 | Rosenblatt | 128/886 |

* cited by examiner

Primary Examiner—Michael A. Brown
(74) Attorney, Agent, or Firm—Mark Clodfelter

(57) ABSTRACT

Circuitry for providing playback of an audio message responsive to activation of a device is provided. The playback circuitry and storage for the voice signal may be provided in the form of a module that plugs into a receptacle in the device, and receives an activation signal and electrical power from the device. In some embodiments, the module may be recorded by an instructor or clinician for instructional or therapeutic purposes and changed as a subject progresses. In other embodiments the module may be prerecorded and selected depending on a situation. Applications range from instructional audio messages in a toothbrush or rental car, to advertising modules responsive to proximity of a potential customer or instructions in a medical device such as a defibrillator or glucose monitor. In another embodiment, the module may record audio responsive to activation of a driver upon which a crime is being committed, such as a carjacking.

20 Claims, 12 Drawing Sheets

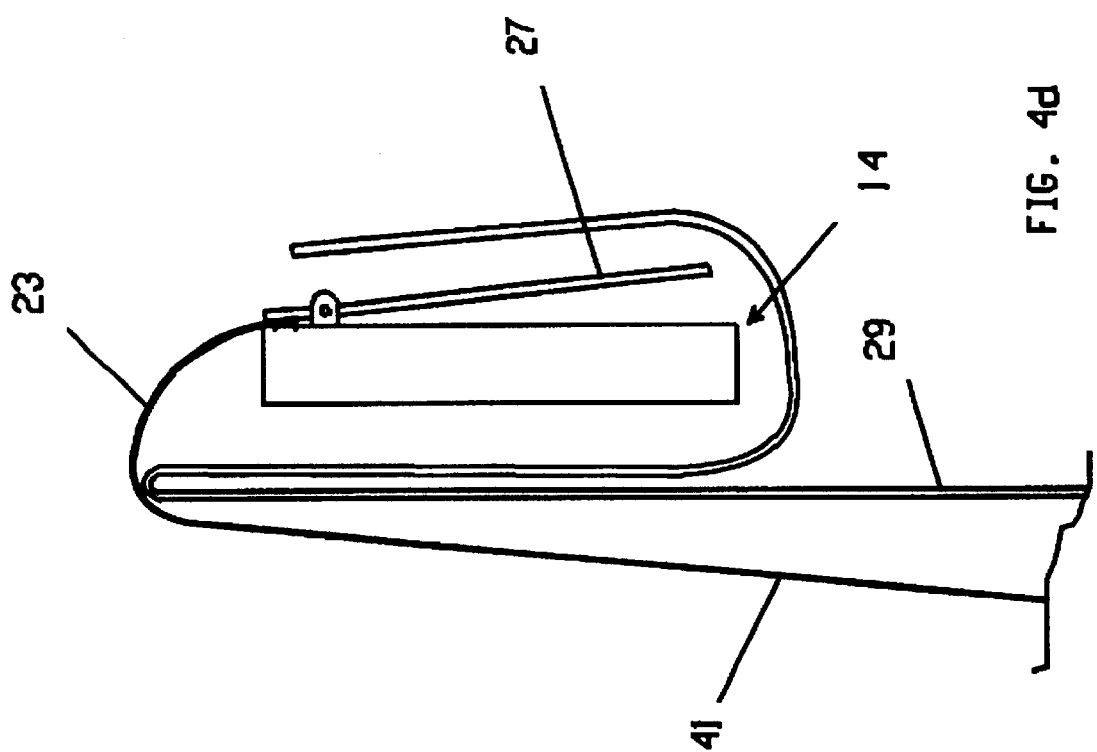

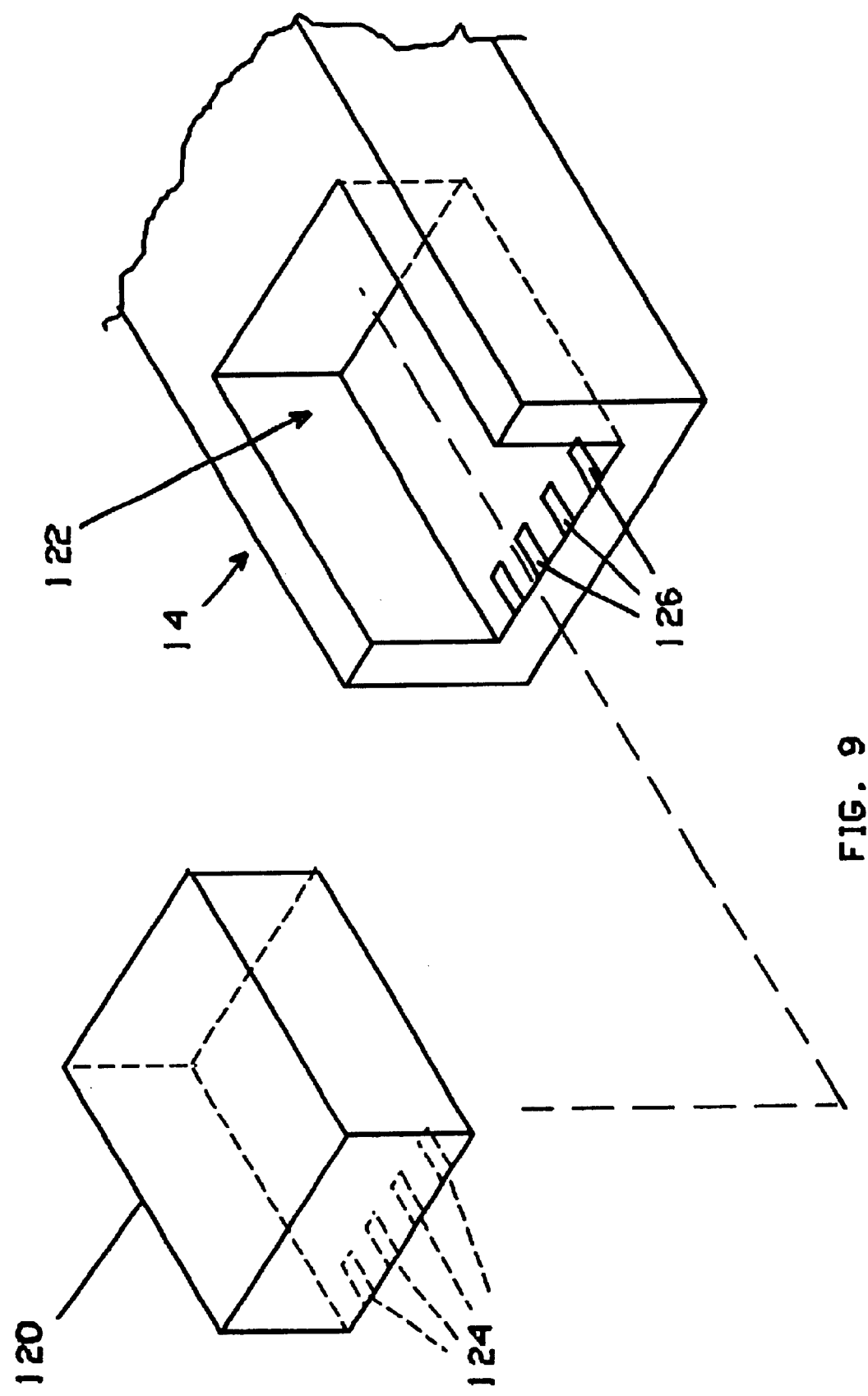

BLADDER AND BOWEL TRAINING SYSTEM WITH REMOVABLE VOICE MODULE SYSTEM

CONTINUING APPLICATION DATA

This application is a continuation-in-part of patent application Ser. No. 08/918,455, filed Aug. 26, 1997, now U.S. Pat. No. 5,845,644 which is a continuation-in-part of patent application Ser. No. 60/025,022, filed Aug. 26, 1996.

FIELD OF THE INVENTION

This invention relates to training aids for training or retraining of bladder and/or anal sphincter muscles of the 20 million or more individuals in the United States who suffer from incontinence. More particularly, this invention utilizes a is disposable, inexpensive carbon impregnated sensor thread in a sensor strip that allows consideration of reusable cloth diapers and inserts which greatly reduces skin disorders and bladder infections while offering the advantage of cost reduction and conservation of space in landfills. In addition, the training aid may incorporate a modular system wherein a re-recordable voice module and receiver for receiving the voice module is adaptable for a variety of purposes.

BACKGROUND OF THE INVENTION

Incontinence is a urologic disorder that results in partial or full loss of control of anal and/or bladder sphincter muscles, reducing or eliminating control over fecal and urine flow, respectively. The American Foundation for Urological Disease (AFUD) reports that more than 50 million individuals suffer from traumatic urologic disorders, of which the National Association for Continence (NAFC) documents 20 million or so suffering from incontinence. Some of these individuals are in nursing homes or hospitals, while others are ambulatory to the point of leading normal lives with the exception of being affected by incontinence.

Incontinence sufferers are generally classified in three major groups; ambulatory adults, geriatric bedridden and juvenile. Specialized treatment is required for each group, with surgery being predominant for ambulatory adults and the geriatric, followed by medication, exercises of the muscles of the pelvic floor, biofeedback, electrical stimulation, and collagen injection. The associated cost of such treatments amounts to something on the order of about 13 billion dollars annually, with much of this cost being borne by Medicare. The National Association for Continence 1996 Spring report, Volume 14, #2 reports the following results after treatment:

2.6% report being cured 9.4% report having a worse condition 41.4% report slight to moderate to greatly improved conditions 46.6% report no change in condition.

From these treatment results, the Medicare burden is completely removed in only 2.6% of cases while 97.4% of these cases remain a financial burden. At the American Urological Association Allied authored by Jan O'Dea of Columbous Urology Inc. of Columbous, Ohio is quoted as stating "Our private urology practice has treated 21 men with continence after radical prostatectomy for localized prostate cancer. 20 of the 21 patients demonstrated improvement, with the majority reporting 75% to 100% satisfaction. 6 patients are totally pad free. Patients began treatment from 3 to 5 years after prostatectomy and had varying degrees of incontinence. Treatment for these patients consisted of a comprehensive approach using behavioral interventions and biofeedback assisted pelvic floor exercises.

Biofeedback is a scientific technique wherein an individual consciously controls a bodily function, such as heartbeat, blood pressure, or certain sphincter muscles, responsive to signals provided by instrumentation. Such instrumentation typically uses adhesive skin patches or straps incorporating electrical terminals that gather electrical information from skin of the patient, and which are manufactured by a number of manufacturers today. In addition, HUMED of Huntsville, Ala., has developed an affordable, portable application specific home/office biofeedback training system to serve an array of patient disorders including depression, incontinence, stress, and stroke. Success is repetitive dependent, necessitating a portable in-home unit.

Applicants system includes a portable computer similar to a laptop computer having a display, sensor package, CD ROM drive, and prerecorded memory voice modules. Accordingly, a patient visits a hospital, clinic, pain center, or other appropriate institution to be evaluated as to specific needs. Upon a determination that Applicants system is an appropriate treatment, the patient is provided the system along with a CD ROM and voice module containing information specific to his/her needs. After a predetermined period of time, the patient revisits the institution for evaluation of progress, at which point the patient may be given another CD ROM and voice module containing different instructions to further treatment. As such, one objective of the instant invention is to offer affordable training or retraining of the bladder and/or anal sphincter muscles that have been impaired by stroke, Alzheimer's disease, prostrate disorders, surgery, child birth, medication side effects, aids, behavioral disorders, learning disabilities and other conditions that necessitate training or retraining of muscles that control voiding of the bowel and bladder.

Aside from the ever present danger of skin and bladder infections, incontinence may rob the individual of self confidence, sleep, extended travel, the joy of physical activity, and often reduces an individual to a disabled condition. This sometimes occurs where an individual uses a gel-type incontinence garment or insert, which garments and inserts being designed to hold a greater quantity of liquid than a non-gel type garment or insert. As a result of the greater capacity of these gel-type devices, a user may become accustomed to the odor of urine, and in turn becoming unaware of the discomfort of others subjected to such odor. The ensuing embarrassment from this situation often drives an individual to become reclusive, in turn placing additional burdens on the state and federal governments, whereas with proper training or retraining of the bowel and bladder sphincter muscles, many of these conditions may be reduced or eliminated, allowing a disabled individual to resume a normal life. In addition, over 19 billion gel-type diapers, inserts and other incontinence garments are used annually, and occupy a significant proportion of landfill space. The materials in these diapers, inserts and disposable garments require something on the order of about 200 years to decompose. Applicants sensor strip may be constructed of readily decomposable materials, allowing use of non-disposable undergarments or diapers which may be washed. A number of incontinence alarms for ambulatory adults, geriatric bedridden and juveniles have been proposed but all are significantly different from Applicants bladder and bowel training system, and none have enjoyed any significant measure of success.

One reason for the lack of success of these prior art alarms may be that most disposable pads used for incontinence alarm systems are cumbersome to wear and difficult to connect. Another reason may be expense of the alarm and disposable pads, which may be considerable where each disposable pad is provided with leads that are connected to a sensor element in the pad, with terminals at the end of the leads for connection to the alarm. Yet another reason may be that many individuals with urinary incontinence tend to "dribble", or constantly leak urine at the same rate as kidney production. In this instance, it is simply too expensive and time consuming to constantly change incontinence garments. As a result, these individuals often simply change their incontinence garments at set times during their waking hours. The problem with this is that the kidneys produce urine at varying rates, meaning that an incontinent individual may ignore a saturated incontinence garment too long, promoting skin rashes or ulceration of the skin. On the other hand, the incontinence garment may be changed before becoming sufficiently wetted to warrant changing, resulting in waste and the attendant cost.

Another problem is that in those devices wherein a sensor strip is used to sense a wet condition of an incontinence garment, such as in U.S. Pat. No. 5,226,928, issued to Johnson, the sensor strip is constructed of a non-variable length. As such, the strip must be long enough to insure adequate length for all individuals. Additionally, due to configuration of the alarm circuitry, shortening the sensor strip would, in one embodiment where a urine battery is formed by the length of the conductors, decrease current provided by the urine battery to a point where the alarm probably would not operate. In the other embodiment, shortening the sensor strip would decrease the available conductor length over which a preselected resistive threshold is established, adversely affecting operation of the alarm.

It is believed that other products were not successful because they were designed, developed and marketed exclusively as alarm systems without the ability to train or retrain bladder and anal sphincter muscles.

Patent references include U.S. Pat. No. 5,226,928 to Johnson as discussed above; U.S. Pat. No. 4,977,906 issued to Disciple, which is intended to be used in conjunction with supervision; U.S. Pat. No. 4,162,490 issued to Hung-Fa is a device affixed to a toilet seat; U.S. Pat. No. 5,043,704 to Blakney discloses a bed wetting alarm; U.S. Pat. No. 4,356,479 to Wilson, and is a bed wetting detector; U.S. Pat. No. 5,036,859 to Brown discloses a bed wetting detector device; and U.S. Pat. No. 4,796,014 issued to Cala activates an alarm that incorporates a time delay so as to not interrupt the act of urination by a baby.

Applicants bladder and bowel training system fulfills all requirements of an affordable, portable, non-invasive, self-contained training system designed to allow the incontinence sufferer to conceal an electronic alarm package having a number of modes of operation anywhere on his/her person. These modes of operation include audible, mechanical, transmitted, verbal, and visible modes that alert a user to inadvertent flow of urine and fecal material. Concealment of the electronics package may be accomplished by simply affixing the electronics package to the front or rear of a diaper or incontinence garment, or the electronics package may be contained in a separate pocket pinned or clipped to clothes of the user. Also, the electronics package may be carried in a pocket of a garment worn by the user, such as a shirt pocket, thereby facilitating a more normal lifestyle of an affected individual. Such concealment is important inasmuch as Applicants system allows the incontinence sufferer to develop self confidence knowing that the system does not draw attention to the individual's disorder. Also, design of Applicants system allows it to be constantly worn in comfort by a user for the purpose of biofeedback training and development of self confidence.

Additionally, the electronics package of the present invention may incorporate a system including a removable voice module and receptacle in a device or system along with circuitry to operate the voice module. In some instances, an amplified voice signal is provided to an audio transducer. This type system has a wide range of uses in a variety of applications.

Accordingly, it is one object of the invention to provide a urinary sensor strip for use by an incontinent individual that is of linear construction and which in operation is insensitive to length. Another object is to provide a urinary sensor strip relatively insensitive to dribbling, which accordingly provides indications only when the incontinence garment needs changing. Yet another object is to provide circuitry which implements a variety of modes of operation depending on needs of the user. Still another object of the invention is to provide a voice memory module that is removably installed in a primary device and which is selectively activated by the primary device. Other objects of the invention will become clear upon a reading of the following specification.

SUMMARY OF THE INVENTION

A system is disclosed for providing an audio message responsive to activation of a device wherein the system includes a circuit for storing and playing back the audio messages, the circuitry being housed in a modular housing having a plurality of electrical contacts for conveying power and signals to and from the circuitry. A receptacle is provided in the device for receiving the module, the receptacle also provided with a set of matching electrical contacts for electrically coupling to the module. Detection of activation of the device energizes the module to play the message.

BRIEF DESCRIPTION OF THE DRAWINGS

FIG. 4d is a broken away view of the sensor strip of FIG. 4c and indicator unit in use.

FIG. 9 is an illustration of a removable voice module of the instant invention.

FIG. 10 is an illustration of indicator unit 14 incorporatable in a fishing lure.

DETAILED DESCRIPTION OF THE DRAWINGS

Figure 1:
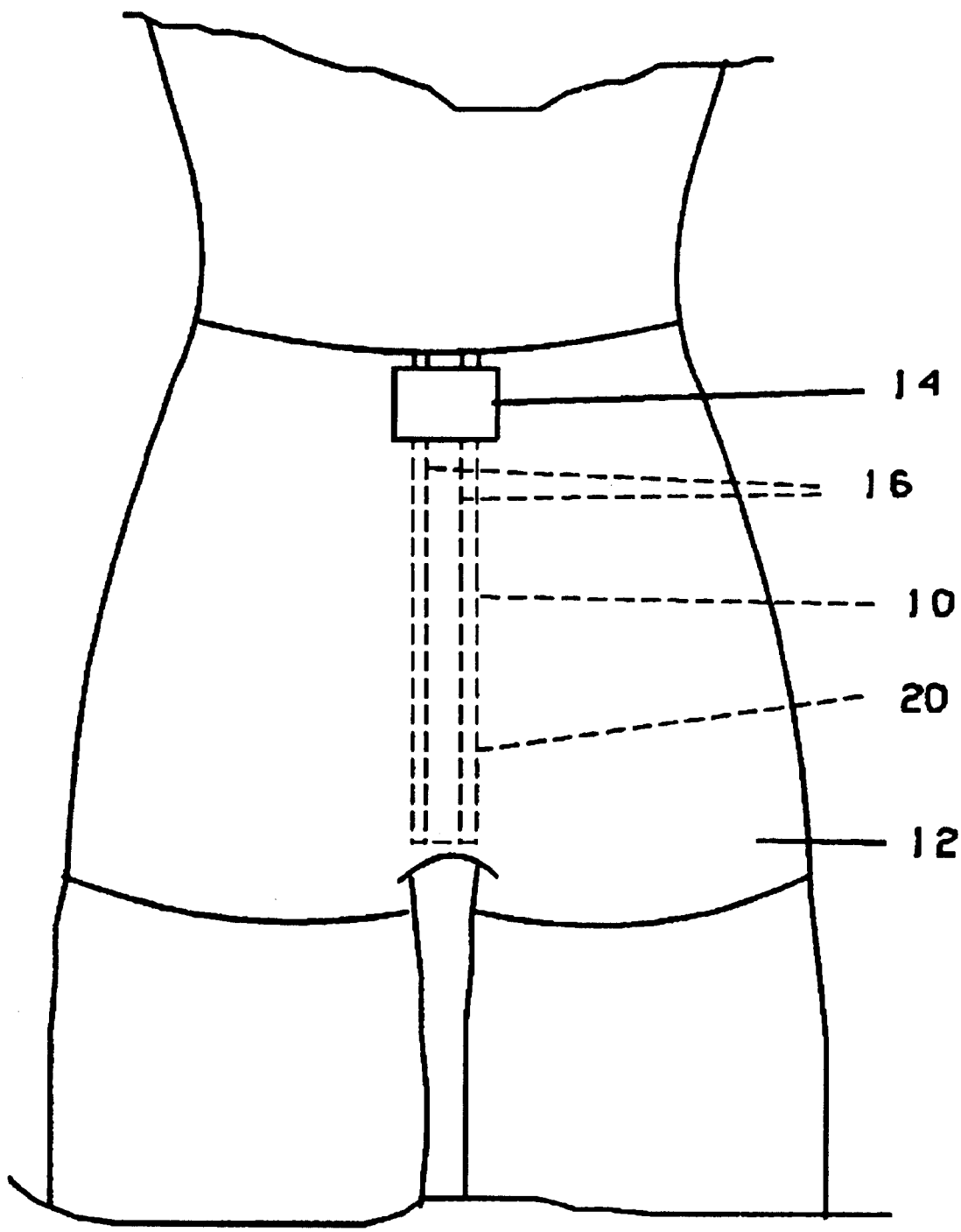
FIG. 1 is an illustration of a user wearing an incontinence garment and sensor strip and indicator unit of the instant invention.

Referring initially to FIG. 1, a view of the instant invention is shown in one of its contemplated uses. Here, a disposable sensor strip 10 (dashed lines) of appropriate length as adjusted for size of a user is positioned between the perianal area of the user and incontinence garment 12. While shown in use with a full-size incontinence garment, strip 10 may also be used in conjunction with incontinence inserts and conventional undergarments and underwear. An electronics package 14 implements various modes of operation to alert the user that voiding is occurring or that the incontinence garment requires changing, as determined by the user. Sensor strip 10 is linearly constructed of an inexpensive, thin, porous substrate material 20 such as a tissue-type paper, cloth, spun or woven material, non-porous sheet material or combinations thereof.

A pair of spaced threads 16 of relatively strong, flexible material, such as cotton, flax, rubber, or a synthetic material, are made electrically conductive as by the addition of a conductive material, such as, but not limited to, carbon. Such conductivity of threads 16 may be of any degree as long as an electrical path created by electrolytes in urine of fecal material bridging threads 16 is detectable by circuitry in unit 14. These conductive threads are available from HUMED INC. located in Huntsville, Alabama, and form conductive sensor elements that are stitched or otherwise imbedded, as by adhesive, lengthwise into the substrate material 20. Garment 12 may be in the form of a conventional undergarment, diaper, or the like used to catch and absorb urine or fecal material of an incontinent individual. Threads 16 in sensing strip 10 serve to sense a wet condition of garment 12, and initiates a variety of alerting responses from electronic package 14 clipped to strip 10.

Figure 2A:
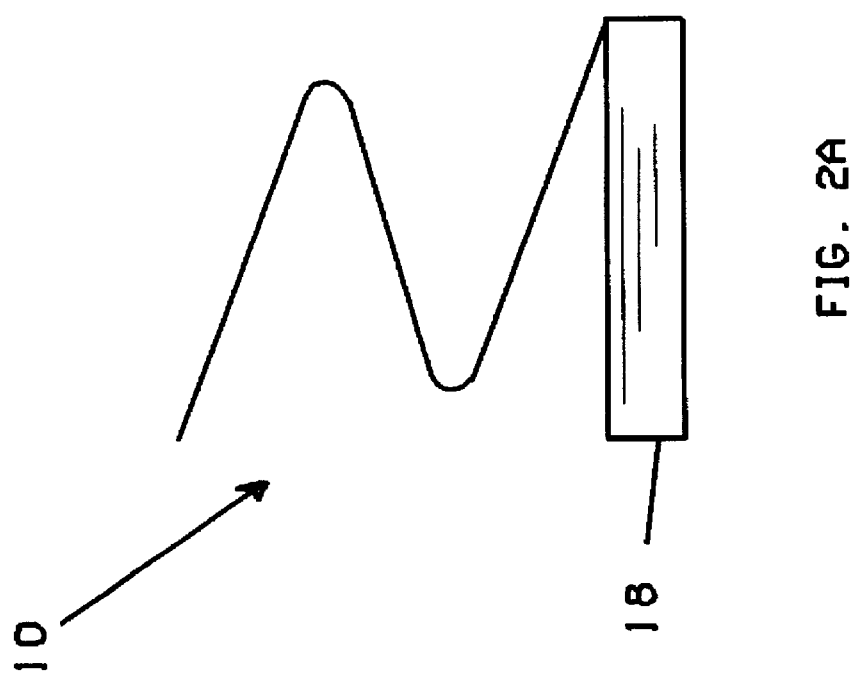
FIG. 2a is an illustration of a length of sensor strip material containing a number of sensor strips packaged in a flat package suitable for carrying in a pocket or purse.
Figure 2:
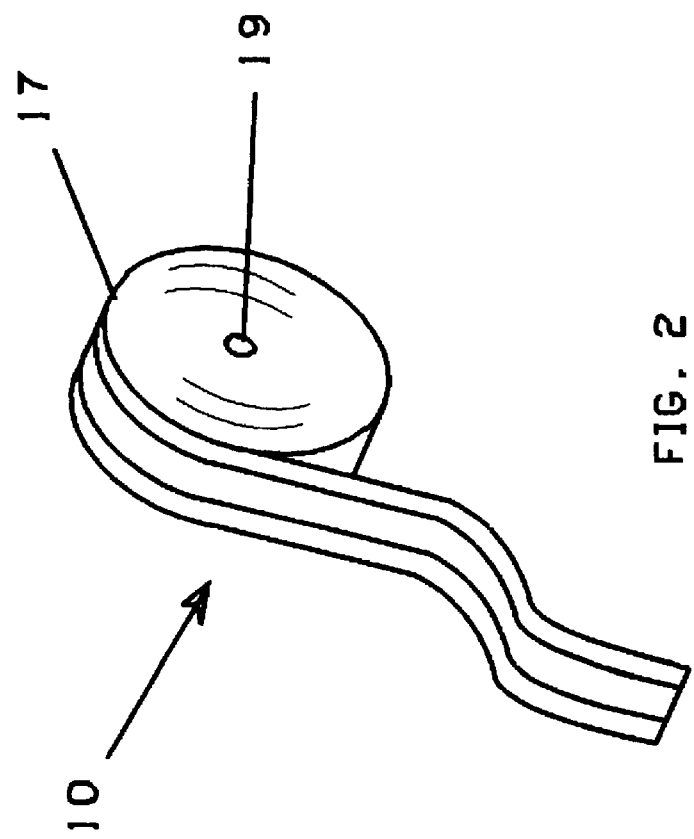
FIG. 2 is an illustration of a roll of sensor strip material suitable for a dispenser and containing a number of sensor strips.

Significantly, as morphology between individuals varies greatly, and as there are no mechanical or electrical length restrictions on the sensor strip, sensor strip 10 may be constructed as a continuous strip and conveniently packaged in a form, such as on a roll 17 or in a flat package 18, as shown in FIGS. 2 and 2a, respectively, which allows the user to simply tear or cut an appropriate length of sensing strip material from a contiguous, packaged length thereof. As such, sensor strip 10 may be field fashioned to accommodate individual needs by selectively cutting a desired length from roll 17 or flat package 18 of sensor strip material. For example, an infant may require a sensing strip of only a few inches in length to extend from the top of the diaper to a point such that the sensing strip completely traverses the perianal area, while a large adult of substantial girth may require a sensing strip three feet or more in length in order for the sensor strip to provide coverage of the same perianal area.

Where the sensor strips are fabricated on roll 17, they may be placed inside a dispenser (not shown) which rotatably supports roll 17 about an axis 19 and which may incorporate a knife edge or other cutting assembly to facilitate cutting a selected length of sensor strip material to form a single sensor strip. This arrangement may be preferable for use in institutions such as hospitals, nursing homes and Veterans Administration Hospitals, where rolls 17 of sensor strip material sized such that numerous, possibly hundreds, of sensor strips may be obtained from a single roll installed in discrete patient rooms or in a central location. As such, and as an important feature of the instant invention, the sensor strips may be sized in length according to individual needs of each patient, eliminating waste related to sizing of the sensing strips. Additionally, by constructing the sensor strips as continuous lengths from which a plurality of sensing strips may be obtained and packaging them on a roll, manufacturing of the strips is greatly simplified, with attendant reduction in manufacturing costs.

Alternately, a sensor strip 10 may be incorporated as a part of an existing or developed incontinence garment or insert or appropriate undergarment. In this embodiment, sensor strip 10 may be sewed directly into an incontinence garment, insert or undergarment, with a covering to shield the conductive threads from skin of the user. A tongue or flap of material containing the conductive threads would be provided in a convenient location, such as the front of the garment, so as to facilitate connection to electronic package 14. Also, two conductive threads may be sewed directly into an incontinence garment, insert or undergarment with a tongue or flap of material containing the threads provided as described.

Figure 3:
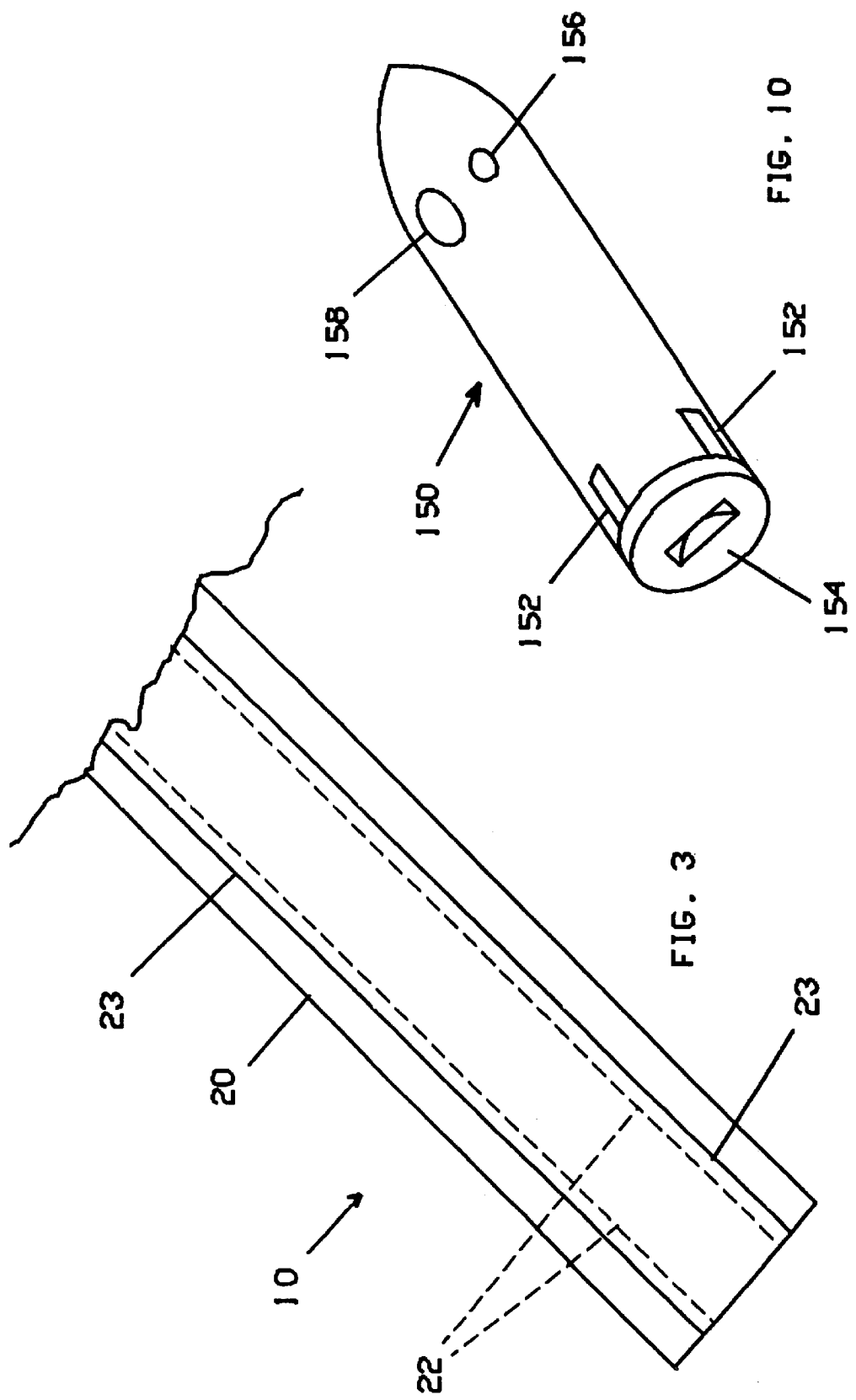
FIG. 3 is an illustration of details of construction of sensor strip material.

The disposable sensor strip is designed for use with all diapers and inserts and all appropriate undergarments. Also, as sensor strip 10 may be constructed of paper tissue-type materials, such a strip 10 may be disposed of in most conventional septic systems. In other instances, sensor strip 10 may allow use of inexpensive non-gel incontinence garments and inserts, which reduce the likelihood of skin disorders and bladder infections while reducing waste deposited in landfills. Of course, gel-filled incontinence garments may also be used where necessary. For packaged lengths containing sufficient strip material to fashion a number of sensor strips therefrom, the substrate length may be about 10 feet or more and constructed having a substrate width of about 4.5 inches or so. As described above, and as shown in FIG. 3, substrate 20 is provided with two spaced, conductive threads 22 which are sufficiently flexible so as to be sewn or stitched lengthwise as shown into substrate 20, or imbedded in the substrate material by other means, such as by an adhesive or strip of material which secures the threads to substrate 20. Threads 22 may be spaced from about 1 to 3 inches apart, and edges of substrate 20 outboard the threads may be folded generally along lines 23 and secured on a side of the substrate material opposite threads 22, covering threads 22 on that side. In use, the exposed sensor threads are positioned adjacent the incontinence garment, with the folded-over edges positioned next to the skin of the user.

Figure 4:
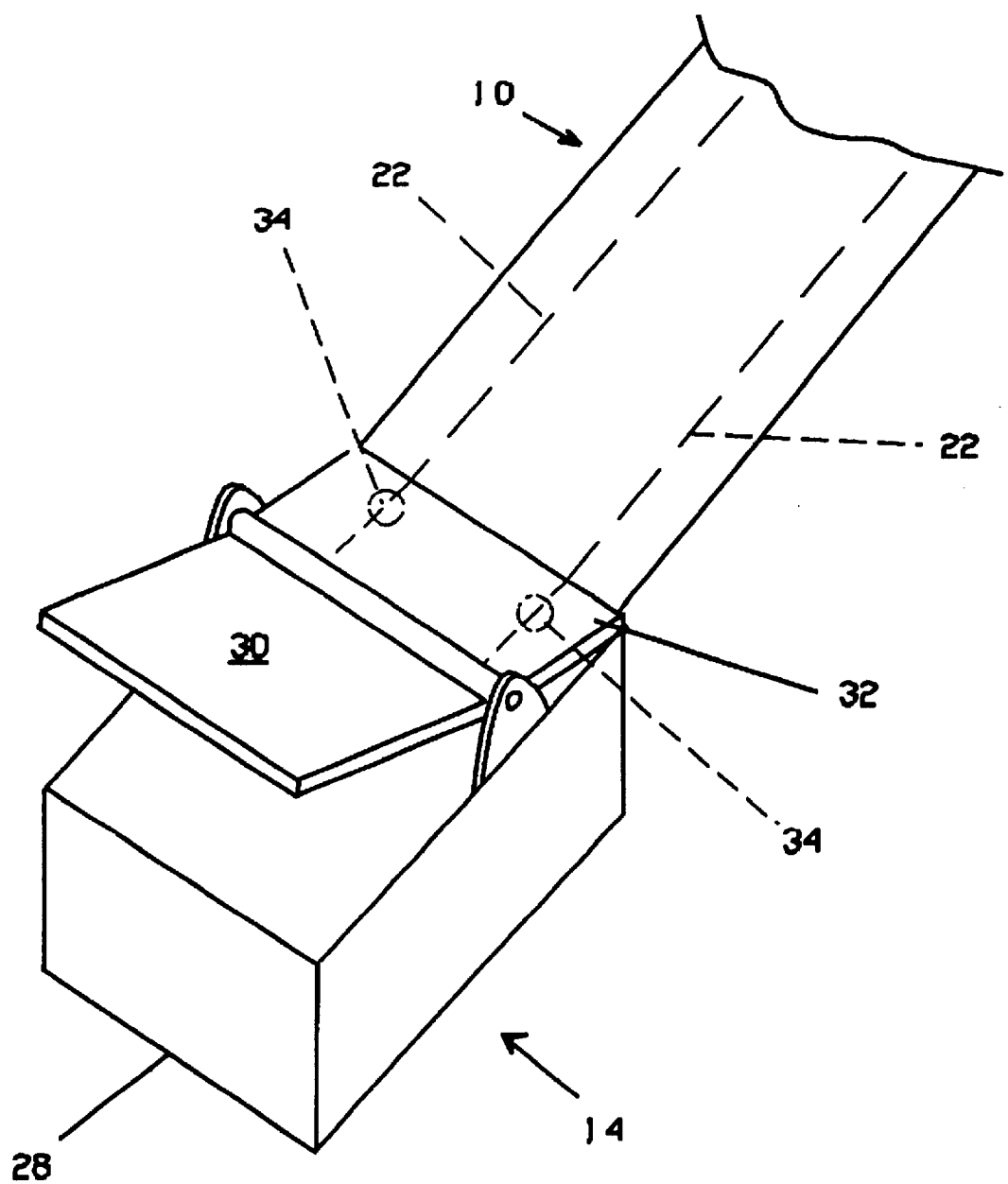
FIG. 4 is an illustration showing construction details of an exterior of an indicator unit 14.
Figure 4A:
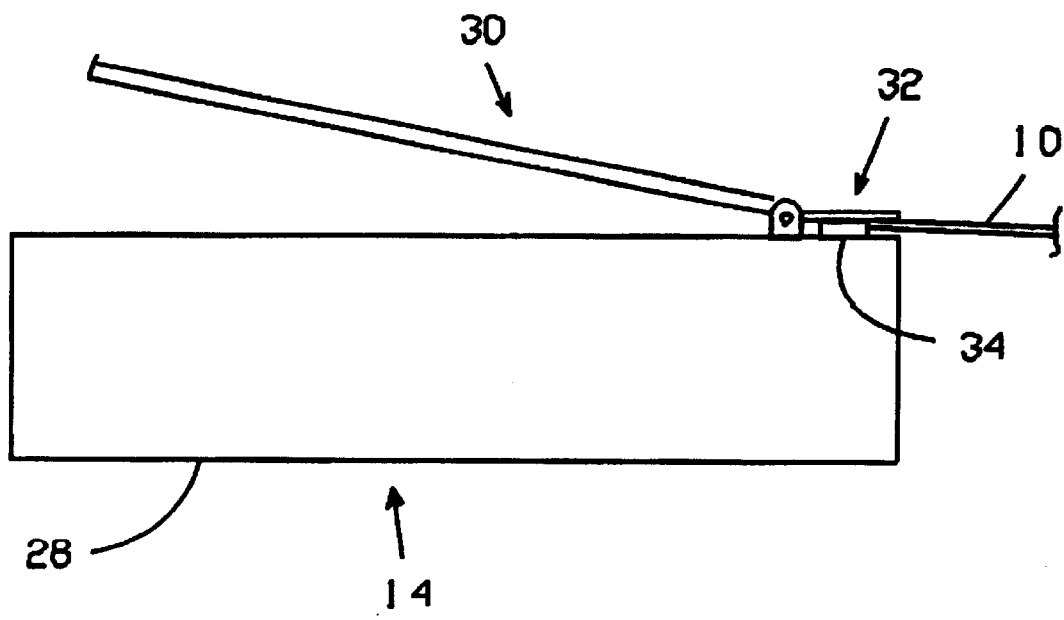
FIG. 4a is an illustration of additional exterior construction details of the indicator unit 14.
Figure 4B:
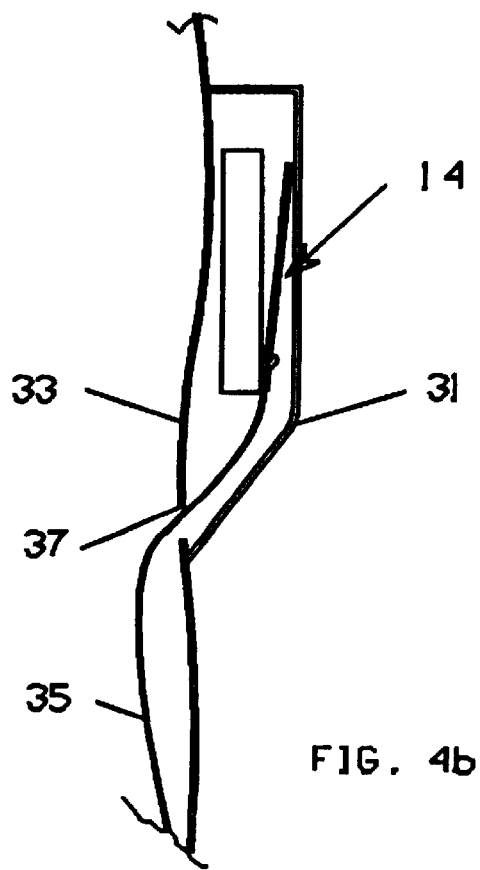
FIG. 4b is a broken away view of indicator unit 14 placed in a pocket of a user.

Electronics package 14 may be provided with a spring-loaded clip 30, as shown in FIGS. 4 and 4a, with a pair of contacts 34 underneath a clamping portion 32 of clip 30 for contacting the respective threads of a selected length of sensor strip material when sensor strip 10 is clamped by clamping portion 32. The spring force of clip 30 may be selected such that clamping portion 32 clamps strip 10 with sufficient force such that no other support is required for electronics package 14. If necessary, clamping region 32, contacts 34 and possibly housing 28 may each or all be constructed with teeth or an abrasive area so that strip 10 is more securely held by clamping region 32. As such, unit 14, being exceedingly small and lightweight, may simply hang by the sensor strip secured only by clamping region 32. In the instance where the users are able to care for themselves, unit 14 may be placed in a pocket of a garment via an opening in the interior pocket lining, with sensing strip 10 being selected of a length so as to permit such location. This eliminates the need for pockets in the incontinence garment or sensing strip and/or cumbersome mounting arrangements for unit 14 as evident in the prior art. In addition, housing 28 of unit 14 is of sealed, waterproof construction so as to prevent any leakage of urine to the interior of unit 14. As such, LED indicators may be sealed by a waterproof compound, such as a silicone sealant, and a sound element, such as a piezoelectric or conventional audio transducer, or moisture-proof speaker, may be mounted behind small openings or a small grille isolated by a sheet material, such as a waterproof plastic positioned between the transducer and interior of housing 28. In the instance where a widened sensing strip is used, the end of the strip may simply be folded longitudinally so that threads 22 are aligned with contacts 34. Also, a separate pouch (not shown) may be provided for holding electronics package 14, which pouch being pinned or clipped at an appropriate location to clothing or incontinence garment of the user and having a suitable slit or opening for receiving sensor strip 10.

Other variants of the sensor strip include coating a side of the strip worn next to the skin with medication, salves, or deodorant substances, such as sodium bicarbonate, and providing an adhesive backing to the strip to prevent the strip from shifting in the incontinence garment. In the instance where an individual or patient has an incontinent condition that causes "dribbling", a continuous or briefly intermittent small spillage of urine, it is desirable not to activate a signal until the incontinence garment needs to be changed. In this instance, spacing of threads 22 may be increased from a normal separation of from about 1–3 inches or so to a wider separation so that a larger area of the incontinence garment or insert must be wetted in order to initiate a response from electronics package 14. In another embodiment, strip 10 may be provided with a selected amount of hydrophobic compound to repel moisture until the incontinence garment needs changing, or a liquid impervious backing may be used so that liquid activating package 14 is forced to seep around edges of the strip 10. Alternately, time delays may be incorporated in electronics package 14 to delay activation of any alert signal to for a predetermined duration, such as one hour, two hours, three hours, etc. This time delay would provide adequate time for the incontinence garment to become sufficiently wetted prior to alerting the user that it needs to be changed.

Figure 4C:
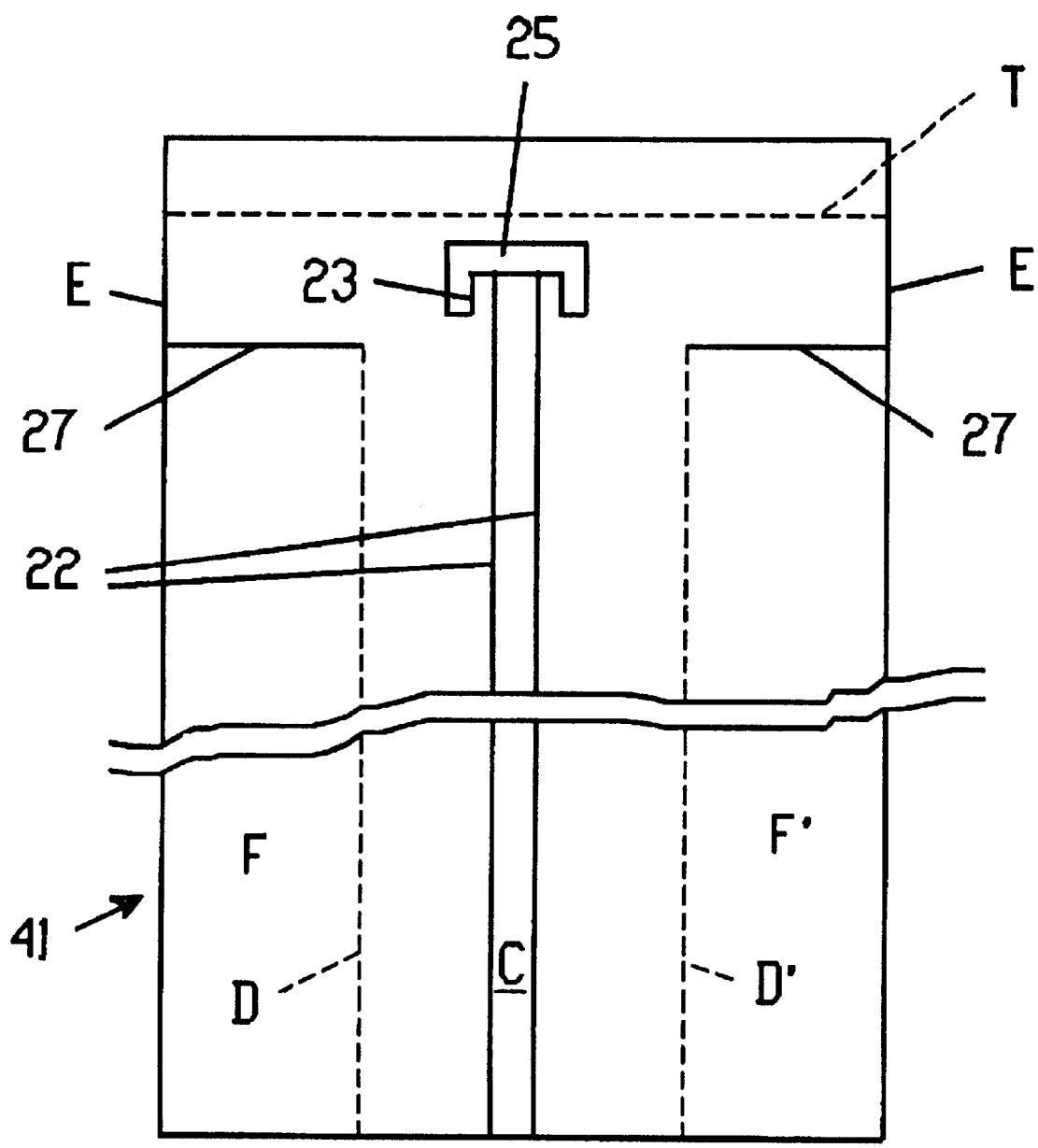
FIG. 4c is another embodiment of a sensor strip wherein a pocket for the indicator unit is formed at one end of the sensor strip.

In an alternate embodiment of the strip 10 as shown, reference is made to FIG. 4c. In this embodiment, a widened strip 41 is constructed with sensing threads 22 terminating at a tongue 23 positioned in an inverted U-shaped cutout 25. Transverse cuts 27 are made as shown on either side of the depending legs of cutout 25 to form downwardly extending flaps F and F', with flap F folded along dashed lines D behind center region C, and flap F' folded along dashed lines D' over center region C. Edges of flaps F and F' are then attached to the center region C, enclosing threads 22 so that they cannot come into contact with skin of a user. Above cutout 25, the upper region is transversely folded along dashed line T over cutout 25, and edges E thereof folded and attached together to form a pocket 27 (FIG. 4d) for receiving unit 14. Constructed as described, tongue 23, being inside the pocket, is clipped to unit 14 as described above, with unit 14 resting in the pocket, which simply hangs outside an incontinence garment 29 inverted from a position shown in FIG. 4c.

Circuitry 14 is a microcontroller based circuit energized when urine or wet fecal material bridges the sensor element, and provides a number of operational modes responsive thereto. These modes include an audio indicator, a blinking LED light, a vibratory indication, and transmission of an RF signal to a receiver that alerts staff of a care-giving institution to a situation requiring changing of an incontinence garment. Significantly, the audio indication may be configured to incorporate a conveniently replaceable or re-recordable voice module which delivers a message usable for training purposes, which may be related to enuresis (nighttime wetting), incontinence, or other types of training when incorporated in other devices, as will be further explained.

Figure 5:
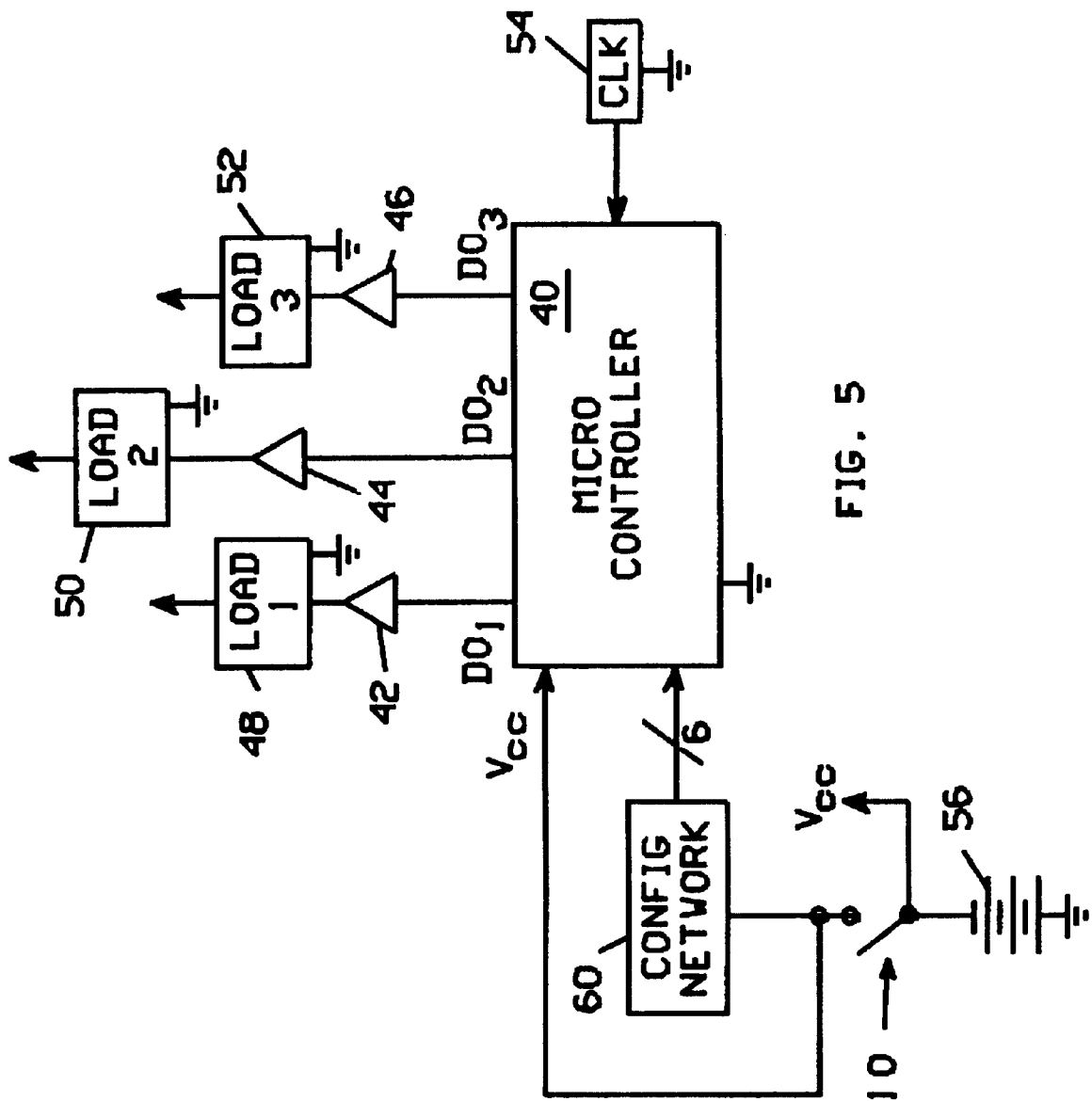
FIG. 5 is a block diagram of indicator unit 14.

Referring now to FIG. 5, a block diagram of a microcontroller-based system is shown which controls electrical operation of the instant invention. Here, three outputs 48, 50, and 52 labeled load 1, load 2, and load 3 are shown for a microcontroller which may implement at least five instructional modes of operation to indicate wet or saturated conditions of an incontinence garment. These outputs may be coupled to activate a vibrator for providing vibration, an audio transducer for providing an audible signal, or a visible indicator for providing a visible indication, such as an LED indicator. Additionally, an RF transmitter may be energized responsive to a wet condition of the incontinence garment to transmit an is RF signal to a receiver or receivers located at a centralized location or on a care-givers person. Further, one of the three outputs may be used to actuate a pre-recorded voice memory module which may be of various time durations, this module removable from unit 14 and being interchangeable with other voice modules having different messages recorded thereon.

As stated, unit 14 may be based on a microcontroller 40 (FIG. 5), such as one of the PIC 16C family of microcontrollers, manufactured by MICROCHIP, located in Chandler, Ariz. These microcontrollers have up to 2K bytes of ROM memory, which may be used to store a system program, and up to 72 bytes of RAM memory, which may be used to store program variables during timing operations. Additionally, as this microcontroller family is of CMOS technology, its low power consumption (less than 2 ma at 5 VDC clocked at 4 Mhz) is ideal for battery powered applications. In this embodiment, it is contemplated to power unit 14 with a 6 volt battery such as one of those found in powering photography equipment, as should be apparent to those skilled in the art.

As described, data outputs DO1, DO2, and DO3 of microprocessor 40 may be used to activate, via buffer amplifiers 42, 44, and 46, a first load 48 which may be an electric vibrator motor, a second load 50 which may be an audio transducer, and a third load 52 which may be an LED indicator, respectively. Alternately, one of loads 48, 50, and 52 may be replaced by an RF transmitter so as to transmit a signal to a receiver located at either a centralized location or on the person of a caregiver, and another of loads 48, 50, and 52 may be replaced by the electronic voice module. An oscillator 54 provides a train of clock pulses to microcontroller 40 at any rate up is to about 20 Mhz, with about 3.5 Mhz being typical. Sensing strip 10 is depicted as a switch, which is closed by urine or fecal material bridging the threads in strip 10, providing power from battery 56 to configuration network 60, microcontroller 40 and other components requiring power. The switching action of strip 10 occurs due to urine being rich in electrically conductive electrolytic compounds. Network 60, which is coupled to data input lines of microcontroller 40, is configured to activate particular ones of data outputs DO1, DO2, and DO3 for selected time intervals.

Figure 6:
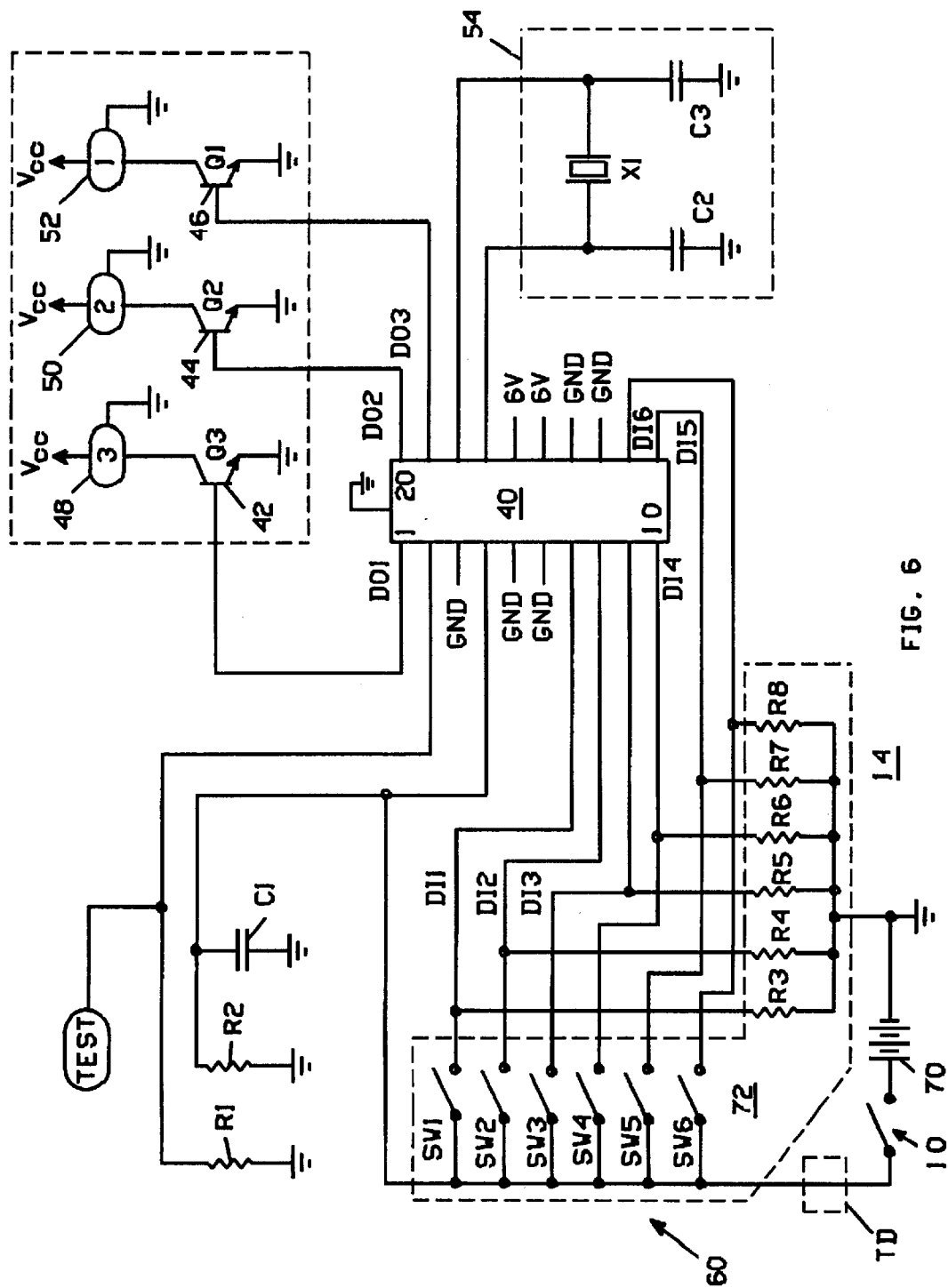
FIG. 6 is a schematic diagram of the block diagram of FIG. 5.

Referring now to FIG. 6, a detailed schematic of the block diagram of FIG. 5 is shown. In this schematic, it is seen that, upon closure of strip switch 10 by urine or fecal material, power and a reference ground potential are provided by battery 70 to microcontroller 40 and all components requiring such potentials. Here, battery power is applied to one conductive thread of sensing strip 10, with the other conductive thread of strip 10 coupled to configuration network 60, the power input of microcontroller 40, and distributed to other components requiring power. Network 60 may include a DIP switch 72 incorporating 6 switches coupled between the switched conductor of sensing strip 10 and a respective one of data inputs DI1–DI6 of microcontroller 40. Coupled between each of DIP switches 72 and the ground reference potential are resistors R3–R8, which serve to develop a voltage drop sufficient to trigger the respective inputs of microcontroller 40. Here, where a higher value of resistance is selected for resistors R3–R8, less current flow through sensing strip 10 would be sufficient to trigger the respective inputs of microcontroller 40, and conversely, where a lower value for these resistors is selected, more current flow would be required through strip 10 in order to develop a sufficient voltage drop to trigger the inputs of microcontroller 40. Thus, sensitivity of the system may be adjusted by varying resistances of resistors R3–R8. By way of example, these resistors may be in the range of about 100K ohms, this selection being fairly sensitive to spilled urine on strip 10 and very conservative of battery power.

Alternately, in place of battery 70, an oscillating or other signal may be applied to one of the conductive threads of sensing strip 10, with the other thread coupled to a detector for detecting the oscillating signal when threads 20 are bridged by conductive material. A HIGH logic level would then be provided to network 72 by the detector, activating the loads as described. Also, in the instance where an individual is dribbling as described above, an adjustable time delay TD (dashed lines) may be located between strip switch 10 and the rest of the circuitry associated with the microcontroller so that upon expiration of the time delay, power is applied to the microcontroller and a HIGH logic level applied to network 72. Alternately, a slower clock pulse may be used in conjunction with a counter and latching decoder to implement the time delay, with the decoder providing a latched output to power the microcontroller and switches 72 responsive to a selected count. As such, and with closure of selected ones of switches 72, when the conductors of sensing strip 10 are shorted by urine or wet fecal material, configuration information is provided to microcontroller 40 through DIP switches 72, this configuration information controlling sequencing and duration of outputs DO1, DO2, and DO3.

The program loaded in ROM memory of microcontroller 40 may use data inputs DI1–DI3 to select which of loads 48, 50, and 52 are to be activated, respectively, with data inputs DI4–DI6 selecting time delays and sequencing of activation of the loads. Constructed as described, and with 6 switches 72, 16 distinct operating modes are made available to the user. The three outputs DO1, DO2, and DO3 may be normally LOW with a common ground, and when activated by the microcontroller, will transition HIGH, enabling the respective one of loads 48, 50, and 52 through a respective buffer amplifier. Where time delay functions are enabled, delays of up to three hours may be selected in one hour increments, after which sequencing of the loads is initiated. After the program sequencing the loads is completed, the microcontroller is placed in a "sleep" mode in order to conserve battery power.

As described, loads 48, 50, and 52 are activated by data lines DO1 controlling load 1, DO2 controlling load 2, and DO3 controlling load 3 via buffer amplifiers 42, 44, and 46, respectively. By way of example, load 48 may be a vibrator, load 50 may be an audio signal, and load 52 may a be LED indicator. In the latter instance, a LED having an internal current-limiting resistor or internal circuitry for causing the LED to blink may be used, or an external current-limiting resistor (not shown) may be used. Alternately, one of the loads may be coupled to a short-range 902–928 Mhz Industrial, Scientific, and Medical (ISM) RF transmitter and which may use multiple frequencies in this range, for notifying caregivers having miniature receivers that a patient has a wetted or soiled garment. Additionally, a computer may be activated by these transmissions in order to record times and dates of instances of incontinence. Inasmuch as space in unit 14 having an RF transmitter is a prime consideration, frequency control devices of layered construction may be arranged in one miniaturized package so that minimal printed circuit board space is required for transmitters that transmit over as many as 5 discrete frequency bands. Such layered frequency control devices are custom manufactured by NPI of Huntsville, Ala.

Figure 7:
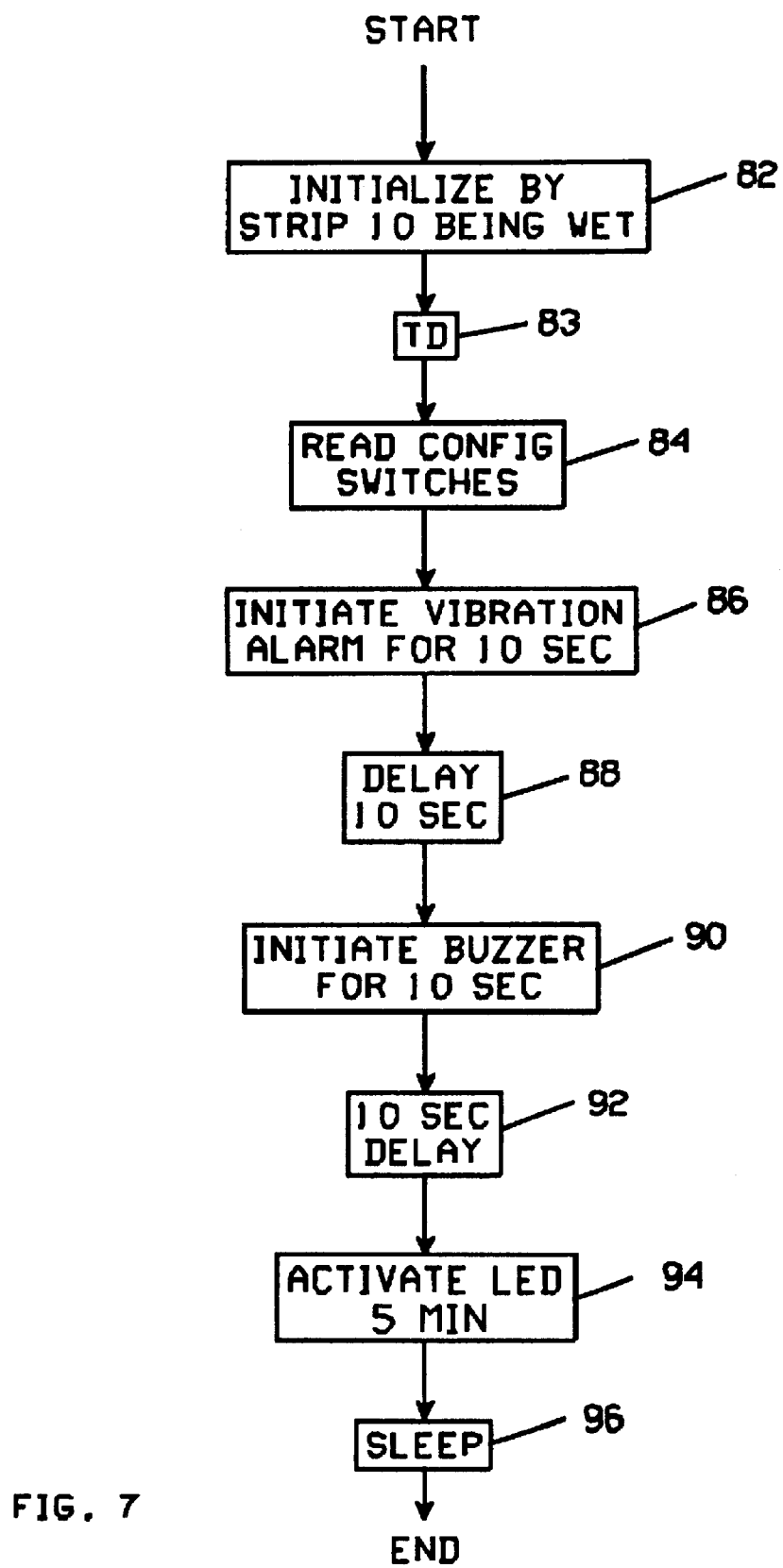
FIG. 7 is a flowchart of one embodiment of a program used to operate unit 14.

The ROM memory of microcontroller 40 is loaded with a program, which may be written in RISC (reduced instruction set computer) language to perform the various functions of the system, an example of one program being shown in the flowchart of FIG. 7. Here, unit 14 is unpowered until sufficient urine is spilled to bridge conductive threads 20, effectively closing sensor switch 10 as shown at box 82. This feature greatly conserves battery power; the circuitry contained in package 14 being unpowered until switch 10 is closed. When energized, microcontroller 40 is initialized as indicated at box 82, clearing and initializing all registers to a predetermined value as is known to those skilled in the art. After power-up initialization of microcontroller 40, the program directs configuration switches 72 to be read at box 84, and an output or outputs to the loads provided based on the settings of configuration switches 72. As shown at box 86, load 48, which may be a vibrator motor, may be initially energized to provide a silent, vibratory indication that alerts a person capable of caring for himself/herself to the fact that his/her incontinence garment has been wetted or soiled. After a duration which may be about 10 seconds or so, the vibration motor is de-energized, and a time delay of about 10 seconds or so is initiated at box 88. After the delay at box 88 expires, the program proceeds to box 90 where load 50 is energized, which load may be an audio signal such as a buzzer, which may be energized for about 10 seconds, after which another time delay of about 10 seconds may be initiated at box 92. After the time delay of box 92 expires, the program proceeds to box 94 where load 52, which may be an LED indicator, is energized for a duration which may be about 5 minutes or so. After this delay expires, the program directs microcontroller 40 to enter a power-conserving sleep mode, as indicated at box 96. Upon changing the incontinence garment and sensing strip 10, power is removed from microcontroller 40, resetting controller 40 in preparation for the next cycle.

This type of program may be used where an individual is bedridden, but able at least at times change his/her own incontinence garment responsive to the vibrating indication. In the instance where a person has a "dribbling" problem, after the sensing strip becomes wet, a time delay TD, at box 83 in the flowchart of FIG. 7, may be started, and which may last any duration selected by the user to allow the incontinence garment to become sufficiently wet to warrant changing. After expiration of the time delay of box 83, the program proceeds to sequence the loads as described for FIG. 7. In the instance where an individual is ambulatory and capable of carrying out the tasks of everyday life, such as being employed, the individual may not need an audible indication due to embarrassment it may cause. In this instance, the vibration indicator and/or the LED indicator may be coupled to a respective one of the outputs of microcontroller 40, and activated as described for a selected period of time as determined by switches 72 and the program stored in ROM memory. The audible indication may be disabled by opening or closing the appropriate ones of switches 72.

Alternately, the time based microprocessor as described along with appropriate software may be incorporated into a wrist-watch type device to be worn on the wrist. In this instance, any of the of the modes of operation as discussed above may occur in any sequence desired. This type device serves as a reminder where particular exercises, such as Kegal exercises, bowel and bladder exercises or any other exercise is to be done at intervals throughout the day. Also, instead of a wrist-worn device, the time based microprocessor may be incorporated into a pocket-carried device, pendant or the like.

Figure 8:
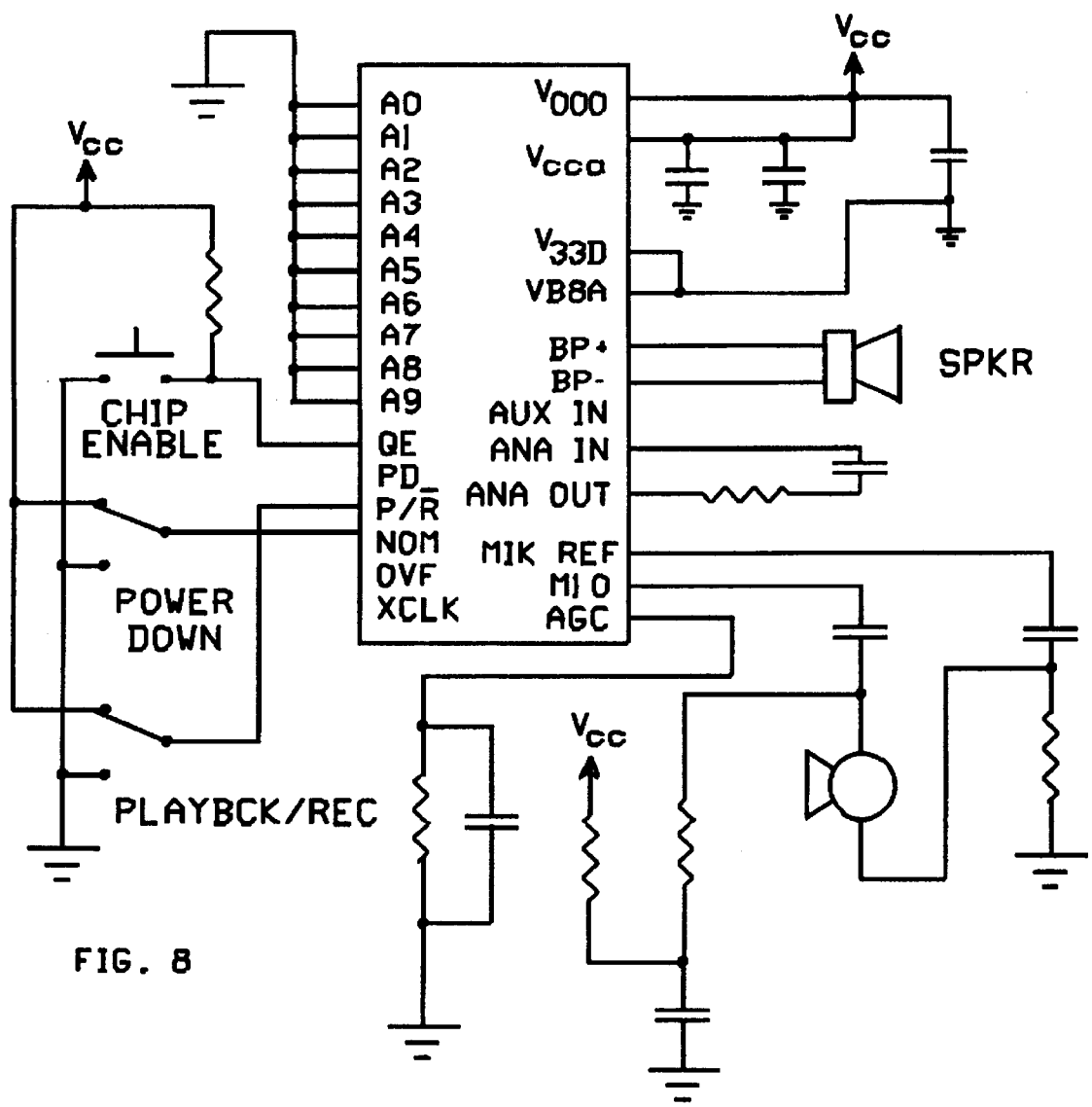
FIG. 8 is a schematic diagram of a voice module of the instant invention.

With respect to the voice module discussed above, reference is made to FIG. 8, which shows by way of example one way of connecting a record/playback integrated circuit (ISD 2500 series devices) available from INFORMATION STORAGE DEVICES of San Jose, Calif. Here, the voice module may be based upon this or similar record/playback devices, with outputs from buffer amplifiers 42, 44, and 46 (FIG. 6) providing signals to operate record and playback modes of the integrated circuit. These integrated circuits record and store up to 120 seconds on a single integrated circuit, these integrated circuits capable of being "daisy chained" together to record and play back longer messages. As such, several minutes of speech, or data, as will be explained, may be recorded in a single inexpensive module. While a specific integrated circuit is discussed and shown, it is to be understood that other similar integrated circuits may be used in conjunction with the system disclosed herein. Additionally, while the integrated circuit as shown in FIG. 8 is configured with both playback and record capabilities, voice modules may be configured for a play-only mode when installed in a primary device. For re-recording play-only voice modules, the modules may be returned to a central facility such as a physician's office where new messages are recorded. In this instance, the modules are inserted into a device containing circuitry including a microphone for providing new messages.

Circuitry similar to that shown in FIG. 8 may be incorporated permanently into electronic package 14, or it may be incorporated into a removable module 120 as shown in FIG. 9. One particular advantage of such a system wherein module 120 is removable, in addition to providing customized voice messages, is related to cost. It is anticipated that the voice modules and structure related to receiving the voice module and circuitry for operating voice module (unit 14) will be inexpensive compared to cost of magnetic tape-based systems. Another advantage lies in the repetitive nature of applicants invention. Here, where a primary device 14 is used several times a day, the message is heard by the user multiple times, constantly reminding the user of particular benefits. For instance, where a user is attempting to stop tobacco consumption, cigarettes or other tobacco products may be placed in a case configured having a removable voice module so that upon opening the case a customized message from a family member is elicited, such as "daddy, please don't smoke, I love you and I want you to be around when I grow up." Such a message could have a powerful effect on an individual attempting to stop smoking. Similarly, a voice module may be incorporated into a scale such that customized messages may be provided to an individual checking his/her body weight. In this instance, reminders may be provided as to what type foods are appropriate or inappropriate for the particular individual.

Module 120 may be held in place in socket 122 by any means as would be known to those skilled in the art, and is provided with an appropriate number of contacts 124 (only 4 shown) as required to transfer the appropriate power levels and signals to module 120 from unit 14. Unit 14 is in turn provided with a corresponding number of contacts 126 coupled to circuitry alike or similar to FIG. 6 which in turn activates the voice circuitry of FIG. 8. If desired, switches 72 (FIG. 6) may be configured so that unit 14 activates module 120 within operational parameters of unit 14.

While voice module 120 is shown used in conjunction with a unit 14 for monitoring incontinence, module 120 may be used in a wide variety of devices where it is desired to provide an application-specific voice message responsive to activation of a primary device. In this application, the primary device corresponding to unit 14 is provided with an appropriate receptacle and power and signal contacts for receiving and energizing the voice module. Additionally, amplification and an audio transducer would be provided in audio applications. Also, instead of being triggered by sensor strip 10, the voice module may be triggered by activation of the primary device or by a proximity switch. For instance, unit 14 may be in the form of a toothbrush or toothbrush holder which receives a prerecorded voice module 120 providing a message of a duration corresponding to a length of time brushing should be performed. For children, this message may be of an entertaining nature, such as a children's story or song, or of an instructional nature, such as how brushing of teeth should be done or a recitation of the multiplication tables. In this instance, where the module contains an educational message such as the multiplication tables, when a particular multiplication table is learned, such as the "times one" table, the module may be removed and either a different module containing the "times two" table inserted into socket 122 or the original module containing the "times one" table re-recorded with the "times two" table.

Another application of such a system would be construction of a removable voice module in medical home-use devices such as a home glucose monitor commonly used by diabetics, the module providing instructions such as how to use the monitor and possibly what the user should do to treat instances of high or low blood sugar. In this instance, and where the glucose monitor provides an indication of high or low blood sugar, the appropriate instructions may be in response to the indication. For example, an indication of high blood sugar may elicit the message of "Your blood sugar is too high, take insulin now" or some other instructional message. Other applications of Applicants invention in medical devices include a portable battery powered microcontroller-based emergency life-saving instruction package located in an emergency life-saving kit such as are found in many public places. Here, operation of the instruction package would be initiated by opening the life-saving kit. Voice modules would be clearly identified as containing instructions for one of several situations such as the victim choking but unconscious, choking and conscious, pulse but no breathing, and no pulse. Other, separate modules may contain life-saving instructions with respect to bleeding, heart attacks, strokes, etc. In this application, the voice modules would be organized so that the module may be quickly located and plugged into an appropriate receptacle as described above. Likewise, a battery powered emergency defibrillator may be provided with a plurality of voice modules each containing instructions for use of the defibrillator in differing medical emergencies. Other medical uses include therapeutic voice messages provided by chiropractors or other rehabilitation professionals involved in program therapy. In these instances the voice module and associated components may be installed or incorporated into chiropractic massage devices or devices that display stretching or strength-developing exercises. In a related device, where an individual is taking a plurality of medications daily, typically in the form of pills or capsules, such medications may be stored in a case incorporating a voice module and associated components so that when the case is opened, instructions are provided as to what medications are to be taken when. Alternately, the case may incorporate a clock wherein a one of several voice modules is activated to indicate which medication is to be taken at that time. In this instance, the voice modules may be recorded by a physician or pharmacist. A related embodiment may be a voice module incorporated in a pendant or pocket device, and indicates when medication is to be taken.

In a voice or pattern recognition system, such as may be installed in a cash register or rental car, a system as described including a removable voice module may be enabled to record voices or other sounds each time a cash register drawer is opened or a driver's seat switch detects a change of drivers. Here, a thief or car hijacker's voice may be recorded as the crime is occurring and the voice module later retrieved for voice comparison/identification in order to identify the perpetrator.

With respect to a keyless entry system, which also may be based on a removable voice module system, each person in a household, building, or user of an automobile, computer or the like wherein access is authorized may record is/her voice on a discrete removable voice module. The individual would also record his/her voice in the keyless entry unit for comparison against the recorded voice in the voice module. As such, the individual would insert his/her prerecorded voice module into the keyless entry unit where the two prerecorded voices are compared, and if they match, then access is granted.

Another application of a voice recognition system in conjunction with a removable memory module system is to establish probable cause when an individual is suspected of being under the influence of mind altering substances, or in a medical context where a person's health may be deteriorating. In this instance, a person's voice is recorded, say when enrolling in school, and the recorded voice saved in a removable module for comparison against the person's voice at a later time in the event the person becomes suspect of being under the influence of a mind altering substance. In a medical context, a person's voice may become more slurred or exhibit other changes in the event of health deterioration. Such changes may be detected by a removable voice memory module system as described.

With respect to automotive applications, a unit for receiving a voice module as described above may be installed in rental cars, the voice module containing directions provided by the rental agency to one or more destinations. A second voice module may contain directions on how to return the car. Similarly, tour instructions may be provided in a plurality of voice modules, with a playback unit mounted in the car and activated by a pushbutton. Additional applications include instructional or promotional messages related to grocery products, which messages being prerecorded in a removable module generally as described and packaged in conjunction with a proximity switch within a grocery store so that when a customer activates the proximity switch, the message is played. A similar use may be found in car sales lots where a removable voice module triggered by a proximity switch may be located in or on an automobile, and delivers a message containing details related to the car that is for sale. Also included would be specific messages for individuals trying to quit smoking cigarettes or maintain certain body weights. Here, specific or progress instructional messages may be developed by health institutions. Other applications include golfing instructions relating to an individual or specific hole of a golf course wherein a proximity switch responsive to a golfer preparing to hit a golf ball initiates operation of a voice module to provide instructions relating to how to play a particular hole.

In another miscellaneous application, cooking instructions may be provided in a plurality of voice modules, one recipe per voice module, with playback components and receptacle mounted to a cooking appliance, stove or integrated in some form of cooking system.

Some other products include a shaving or makeup mirror typically having lights around a periphery thereof, and which delivers a message upon activation of the lights. The message may address any problem or disorder the user may have, such as gambling, depression and anxiety. Here, a removable voice module as described above would be inserted into an appropriate receptacle in the mirror, and would contain messages of therapeutic or inspirational content. Also, messages of instructional nature may be recorded on a voice module as described above and installed in an appropriate receptacle in computers in order to assist individuals in becoming computer literate. The voice module would be re-recorded progressively as the individual became increasingly computer literate.

In yet another embodiment of the invention, and referring to FIG. 10, the microcontroller circuitry of FIGS. 5 and 6 may be incorporated into a fishing lure. Here, the circuitry may be constructed so as to be fitted into a cylindrical housing 150, the cylindrical housing in turn being insertable into a soft flexible lure such as a frog or fish. Alternately, the circuitry may be permanently incorporated into a finished lure. Contacts 152 corresponding to the conductive threads of sensor strip 10 are provided on the exterior of the cylinder in a location that would be exposed to water so that the circuitry becomes activated when the lure is thrown into a river, lake, etc. A removable threaded cap 154 in conjunction with an O-ring seal may be used to sealably enclose a battery compartment, which may receive a 6 volt battery as described above, an N-sized alkaline battery, a AAA sized battery, or a plurality of button-type batteries. When activated, the program may be configured to energize one or more LEDs 156, a piezoelectric buzzer 158, and a vibrator located inside cylinder 150. Any sequence may be used for the LEDs, buzzer and vibrator, such as one wherein the LEDs are illuminated in a blinking mode for about 5 seconds followed by a 10 second delay. The vibrator may then be activated for about 2 seconds, followed by another 10 second delay after which the buzzer may be activated for about 3 seconds. A longer delay may then be provided, such as 30–40 seconds, after which the program repeats until battery power is removed by removing the lure from the water. Alternately, the circuitry may be incorporated into a lure such as a "plug"-type lure without being removable, as should be apparent to one skilled in the art. Further, effectiveness of the lure may be enhanced by the electrical field generated by current flowing between contacts 152, it being understood that certain game fish are sensitive to such electrical fields.

In a related embodiment, a voice memory module as described in the foregoing and in conjunction with amplification and an audio transducer may be incorporated in a game animal lure. In this instance, the lure may be activated at a particular time or after a preset time delay, and also be provided with movement capability, and where desired, scent projection. Thus, lures that have the appearance of deer, frogs, turkeys, ducks, etc. may be made to move and project scent while emitting an animal call.

In an application related to collecting data, a removable memory module system as described may be used where shock and vibration are a concern, such as in dams, railroads, bridges and other infrastructure constructions. Here, conventional shock and vibration measuring devices may be outfitted with the removable memory modules system so that vibration and shock may be recorded for future reference. In this system, time-coded information would be included along with the date so that episodic vibration and shock may be correlated with time.

Having thus described my invention and the manner of its use, it is apparent that incidental changes may be made thereto that fall within the scope of the following appended claims, wherein I claim:

What is claimed is:

1. A system for providing an audio message responsive to activation of a device comprising:

circuitry for storing and playing back said audio message, a housing for containing said circuitry, said housing provided with a first set of electrical contacts for conveying power and signal levels to and from said circuitry, a receptacle associated with said device for coupling said housing to said device, said receptacle provided with a second set of electrical contacts, one of each of said second set of electrical contacts contacting a respective one of said first set of electrical contacts, activation means responsive to activation of said device so that upon activation of said device, said circuitry is energized to play said audio message.

2. A system as set forth in claim 1 wherein said receptacle is incorporated in an electronics package of a moisture sensing strip disposed to be incorporated in an incontinence garment.

3. A system as set forth in claim 2 wherein said receptacle is incorporated in an operating area of a vehicular contrivance.

4. A system as set forth in claim 2 wherein said receptacle is incorporated in a keyless entry system.

5. A method as set forth in claim 3 wherein said energizing means is provided in a driver seat switch of a automobile, and enables recording of said audio message responsive to changing drivers of said automobile.

6. A system as set forth in claim 1 wherein said circuitry for storing and playing back said audio message further comprises recording means for recording said audio message.

7. A system as set forth in claim 1 wherein said receptacle is incorporated in a toothbrush.

8. A system as set forth in claim 1 wherein said receptacle is incorporated in a medical device.

9. A system as set forth in claim 8 wherein said medical device is a glucose monitor.

10. A method as set forth in claim 8 wherein said medical device is an emergency defibrillator.

11. A method as set forth in claim 8 wherein said medical device is a chiropractic device.

12. A system as set forth in claim 1 wherein said receptacle is incorporated in a cigarette case.

13. A method as set forth in claim 1 wherein said receptacle is incorporated in an automobile, with said circuitry for playing back said audio message energized by a pushbutton.

14. A system for providing an audio message responsive to activation of a device comprising:

a separate, discrete housing, circuitry within said housing for storing and playing back an audio message, a first set of electrical contacts on an exterior side of said housing for conveying power and signals to said circuitry, a receptacle in said device for removably receiving said housing, said receptacle having a second set of electrical contacts for contacting a respective one of said first set of electrical contacts, whereby said housing is removable and replaceable within said housing, activation means responsive to activation of said device so that upon activation of said device, said circuitry is energized to play said audio message.

15. A system as set forth in claim 14 wherein said device is a medical device, and said audio message includes instructions for operating said medical device.

16. A system as set forth in claim 14 wherein said device is a toothbrush.

17. A system as set forth in claim 16 wherein said audio message is of a duration sufficient for adequate brushing or one's teeth.

18. A device for replicating an audio message system comprising:

a housing, audio storage and playback circuitry mounted in said housing, said circuitry provided with a first set of electrical contacts for at least providing power and an energizing signal to said circuitry, a mating socket in said device for removably receiving said housing, said socket provided with a second set of electrical contacts physically communicating with said first set of contacts for conveying said power and said energizing signal to said circuitry, a switch associated with said device for energizing said audio circuitry.

19. A device as set forth in claim 18 wherein said switch is a proximity switch.

20. A device as set forth in claim 18 wherein said audio and playback circuitry includes circuitry for recording said audio message.

* * * * *